(12) United States Patent
Wang et al.

(10) Patent No.: US 12,007,394 B2
(45) Date of Patent: Jun. 11, 2024

(54) BIOMARKER FOR PROGNOSIS OF THYROID CANCER

(71) Applicant: Chih-Yuan Wang, Taipei (TW)

(72) Inventors: Chih-Yuan Wang, Taipei (TW); Tien-Chun Chang, Taipei (TW); Pei-Jie Huang, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 371 days.

(21) Appl. No.: 16/638,157

(22) PCT Filed: May 15, 2018

(86) PCT No.: PCT/IB2018/053374
§ 371 (c)(1),
(2) Date: Feb. 11, 2020

(87) PCT Pub. No.: WO2019/053521
PCT Pub. Date: Mar. 21, 2019

(65) Prior Publication Data
US 2021/0373025 A1    Dec. 2, 2021

Related U.S. Application Data

(60) Provisional application No. 62/650,171, filed on Sep. 18, 2017.

(51) Int. Cl.
*G01N 33/574*    (2006.01)
(52) U.S. Cl.
CPC . *G01N 33/57488* (2013.01); *G01N 33/57407* (2013.01)
(58) Field of Classification Search
CPC .. G01N 33/57407; A61P 35/00; C12Q 1/6886
See application file for complete search history.

(56) References Cited

U.S. PATENT DOCUMENTS

| 8,541,170 | B2 | 9/2013 | Kennedy et al. |
| 2010/0131432 | A1* | 5/2010 | Kennedy ............... A61B 50/30 435/6.12 |
| 2011/0275065 | A1* | 11/2011 | Walfish ............ G01N 33/57407 436/64 |
| 2014/0024548 | A1 | 1/2014 | Singh et al. |
| 2016/0146799 | A1 | 5/2016 | Robinson et al. |

FOREIGN PATENT DOCUMENTS

| CN | 103384828 | 11/2013 |
| CN | 105039523 | 11/2015 |
| CN | 107110851 | 8/2017 |

OTHER PUBLICATIONS

Ringel (Thyroid, 21:487-492, 2011.*
Vlasov et al J Thyroid Res, 2016:9276402, 2016.*
International Search Report and Written Opinion for International Application No. PCT/IB2018/053374 mailed on Sep. 12, 2018, 9 pages.

* cited by examiner

*Primary Examiner* — Mark Halvorson
(74) *Attorney, Agent, or Firm* — Amin, Turocy & Watson, LLP

(57) ABSTRACT

The present disclosure provides a method of prognosis of thyroid cancer including obtaining an exosome from a subject who had received a therapy of thyroid cancer such as thyroidectomy, and detecting whether thyroglobulin is present in the exosome. Moreover, the present disclosure provides the use of urinary exosomal thyroglobulin in being a non-invasive, reproducible, convenient, serial, and accurate follow-up marker for patient with thyroid cancer.

11 Claims, 14 Drawing Sheets
Specification includes a Sequence Listing.

SEQUENCE LISTING

```
<160> NUMBER OF SEQ ID NOS: 2

<210> SEQ ID NO 1
<211> LENGTH: 11
<212> TYPE: PRT
<213> ORGANISM: Homo sapiens
<220> FEATURE:
<221> NAME/KEY: PEPTIDE
<222> LOCATION: (1)..(11)

<400> SEQUENCE: 1

Phe Leu Ala Val Gln Ser Val Ile Ser Gly Arg
1               5                   10

<210> SEQ ID NO 2
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 2

Ile Ala Leu Asp Phe Gln Arg
1               5
```

BIOMARKER FOR PROGNOSIS OF THYROID CANCER

CROSS REFERENCE TO RELATED APPLICATIONS

This application claims priority to U.S. Provisional Application Ser. No. 62/560,171, filed Sep. 18, 2017, which is herein incorporated by reference in its entirety for all purposes.

BACKGROUND

1. Field of the Invention

The present disclosure relates to a practical and reliable biomarker for the prognosis of thyroid cancer in a subject, particularly in a subject with ablative therapy of thyroid cancer.

2. Description of Related Art

Thyroid cancer is the most common type of cancer of the endocrine system. Although most thyroid cancers can be treated and are considered as low-grade endocrine malignancies, there has been an increase in incidence rates over the past years. In fact, it is the most rapidly increasing cancer in the US in the past three decades. In addition, thyroid cancer occurs in all age groups and unlike most of the other adult cancers, it is usually diagnosed at a younger age, most frequently among people aged 45-54.

Most thyroid cancer patients receive thyroidectomy with ablative radioactive iodine therapy. While the prognosis for most thyroid cancer patients is usually good, the rate of recurrence can be up to 30%, and recurrences can occur even decades after the initial diagnosis. Therefore, thyroid cancer patients usually receive regular follow-up examinations to detect whether the cancer has re-emerged, and this monitoring continues throughout the patient's lifetime. Hence, with the occurrence of thyroid cancers at relative younger age, the period for follow-up and recurrence monitoring thyroid cancer patients can last up to several decades.

Thyroid cancer patients, after receiving thyroidectomy with ablative radioactive iodine, are followed with thyroid ultrasonography and serial serum thyroglobulin evaluation. In the current practice, serum thyroglobulin is considered as the pivotal biomarker for detecting possible residual tumors or recurrence of thyroid cancer. Generally, postoperative serum thyroglobulin suggests distant metastases. Low-risk patients are typically defined as having non-stimulated postoperative serum thyroglobulin less than 0.4 ng/mL, or thyroid hormone withdrawal thyroglobulin of less than 1.0 ng/mL. However, costly recombinant human thyrotropin (rhTSH) is often required to stimulate serum thyroglobulin for detecting local recurrence or distant metastasis, even though the stimulation may not always result in a detectable serum thyroglobulin. Thus, a more reliable biological marker and a more sensitive method for determining the prognosis of thyroid cancer are in need.

SUMMARY

Herein, the object of the present disclosure is therefore to provide a biomarker and a method to prognosticate the development or recurrence of thyroid cancer in a subject.

In an aspect of the present disclosure, a method for the prognosis of thyroid cancer in a subject in need thereof is provided. The method comprises obtaining an exosome from the subject, and detecting whether thyroglobulin is present in the exosome.

In one embodiment of the present disclosure, the subject had been identified as a thyroid cancer patient. In another embodiment of the present disclosure, the subject had been identified as a thyroid cancer patient who had received a therapy of thyroid cancer. In yet another embodiment of the present disclosure, the therapy of thyroid cancer may be selected from the group consisting of total thyroidectomy, partial thyroidectomy, thyroid remnant ablation with radioactive iodine, target therapy and a combination thereof. In yet another embodiment of the present disclosure, the method is carried out following the therapy of thyroid cancer of the subject. In a further embodiment of the present disclosure, the method is carried out over a period of time in the regular follow-up of the thyroid cancer patient.

In one embodiment of the present disclosure, the thyroid cancer may be selected from the group consisting of follicular thyroid cancer, follicular variant papillary thyroid cancer, papillary thyroid cancer, medullary thyroid cancer, Hurthle cell cancer, anaplastic thyroid cancer, and a combination thereof. In another embodiment of the present disclosure, the thyroid cancer is follicular thyroid cancer or papillary thyroid cancer.

In one embodiment of the present disclosure, the presence of thyroglobulin in the exosome is detected by peptide sequencing with mass spectrometry.

In one embodiment of the present disclosure, the exosome is isolated from a sample of bodily fluid of the subject. In another embodiment of the present disclosure, the sample may be chosen from urine, plasma and serum. In yet another embodiment of the present disclosure, the sample is urine.

In one embodiment of the present disclosure, the method further comprises isolating the exosome from the sample by the process selected from the group consisting of size exclusion chromatography, density gradient centrifugation, differential centrifugation, nanomembrane ultrafiltration, immunoabsorbent capture, affinity purification, microfluidic separation, and a combination thereof. In another embodiment of the present disclosure, the exosome is isolated from the sample by density gradient centrifugation.

In one embodiment of the present disclosure, the method further comprises diagnosing the subject with recurrent thyroid cancer when the presence of thyroglobulin in the exosome is detected. In another embodiment of the present disclosure, the method further comprises administering a thyroid cancer treatment to the diagnosed subject. In yet another embodiment of the present disclosure, the thyroid cancer treatment is chosen from radioactive iodine, target therapy and a combination thereof.

In another aspect of the present disclosure, a method of evaluating a therapy of thyroid cancer is provided. The method comprises obtaining an exosome from a subject who had received the therapy of thyroid cancer, and detecting whether thyroglobulin is present in the exosome, wherein the level of thyroglobulin in the exosome is indicative of the efficacy of the therapy of thyroid cancer.

In one embodiment of the present disclosure, the presence of thyroglobulin in the exosome is indicative of thyroid cancer recurrence.

In one embodiment of the present disclosure, the exosome is obtained from a sample of bodily fluid of the subject. In yet another embodiment of the present disclosure, the exosome is obtained from a urine sample.

In one embodiment of the present disclosure, the method further comprises administering a thyroid cancer treatment to the subject when the presence of thyroglobulin in the exosome is detected. In another embodiment of the present disclosure, the thyroid cancer treatment is chosen from radioactive iodine, target therapy and a combination thereof.

The biomarker and the method of the present disclosure provide an early detection of thyroid cancer recurrence by detecting an increase in the trend of thyroglobulin level in exosome isolated from bodily fluid of the subject. In addition, the biomarker and the method of the present disclosure can realize a practical and reliable prognostication for thyroid cancer recurrence in patient whose serum thyroglobulin is undetectable.

BRIEF DESCRIPTION OF THE DRAWINGS

In the accompanying drawings preferred embodiments of the present disclosure are shown in which.

DETAILED DESCRIPTION

Figure 1A:
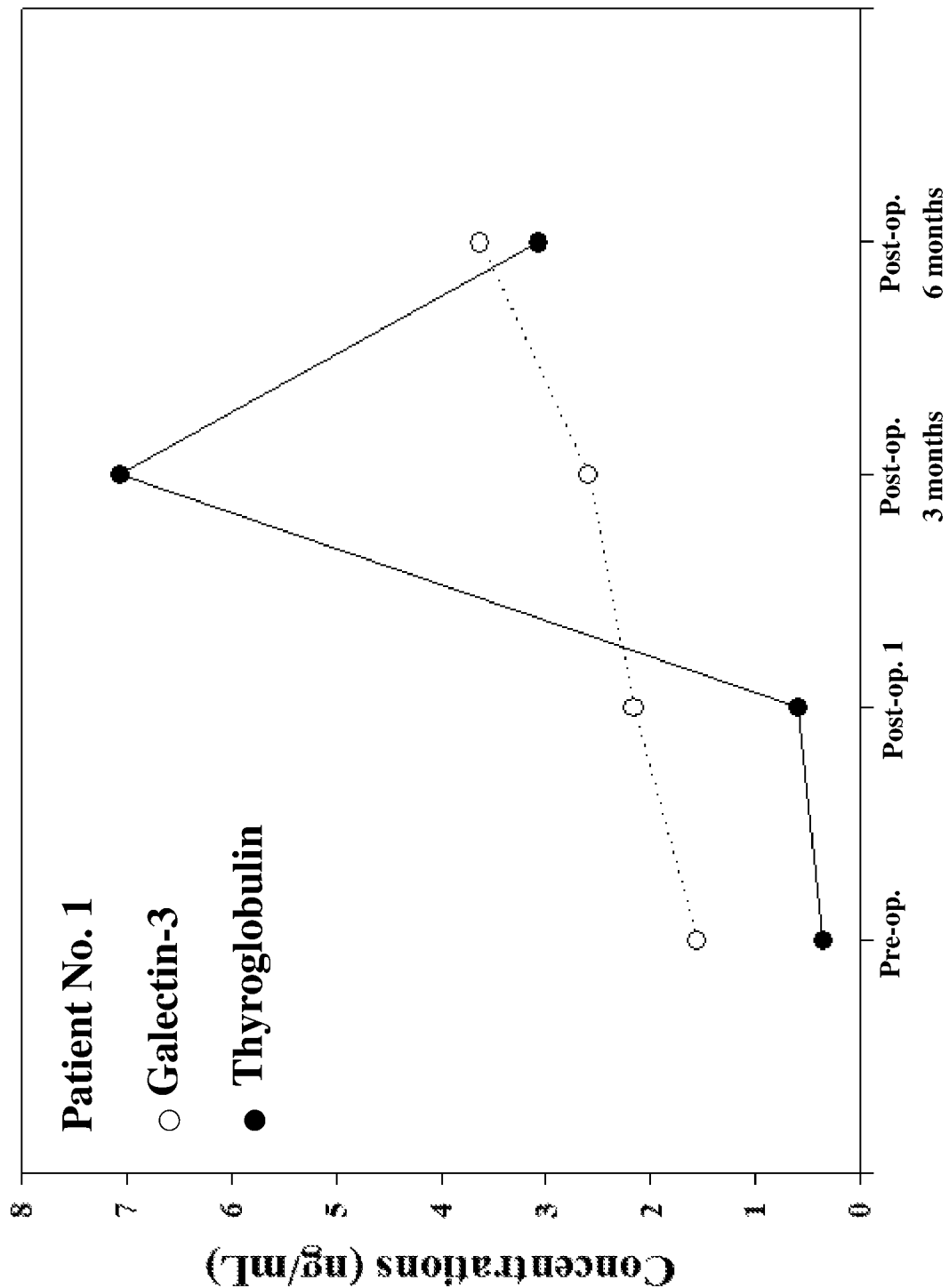
FIGS. 1A-1M show the trends of urinary exosomal protein levels in individual patient before and after operation.
Figure 1B:
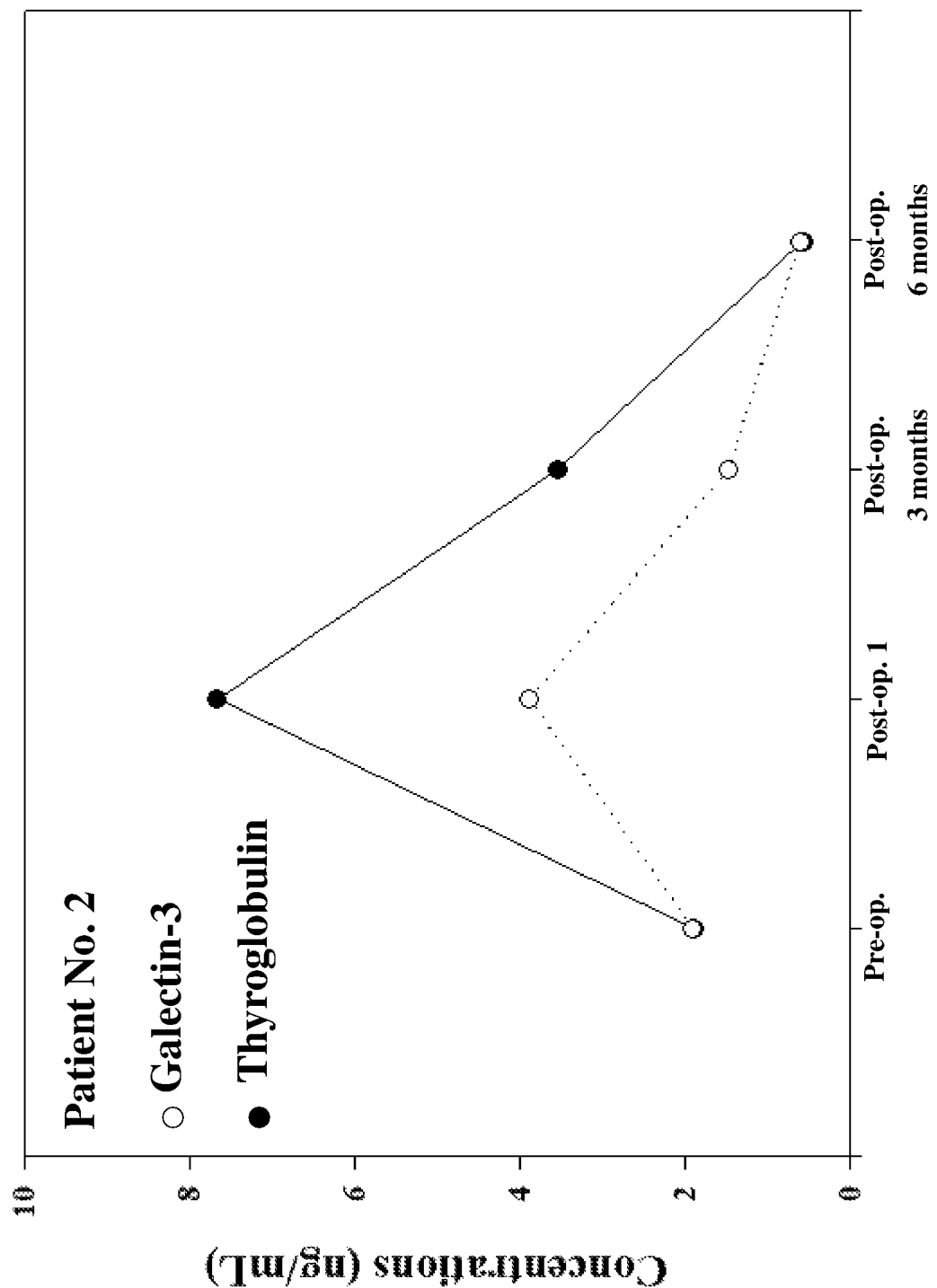
Figure 1C:
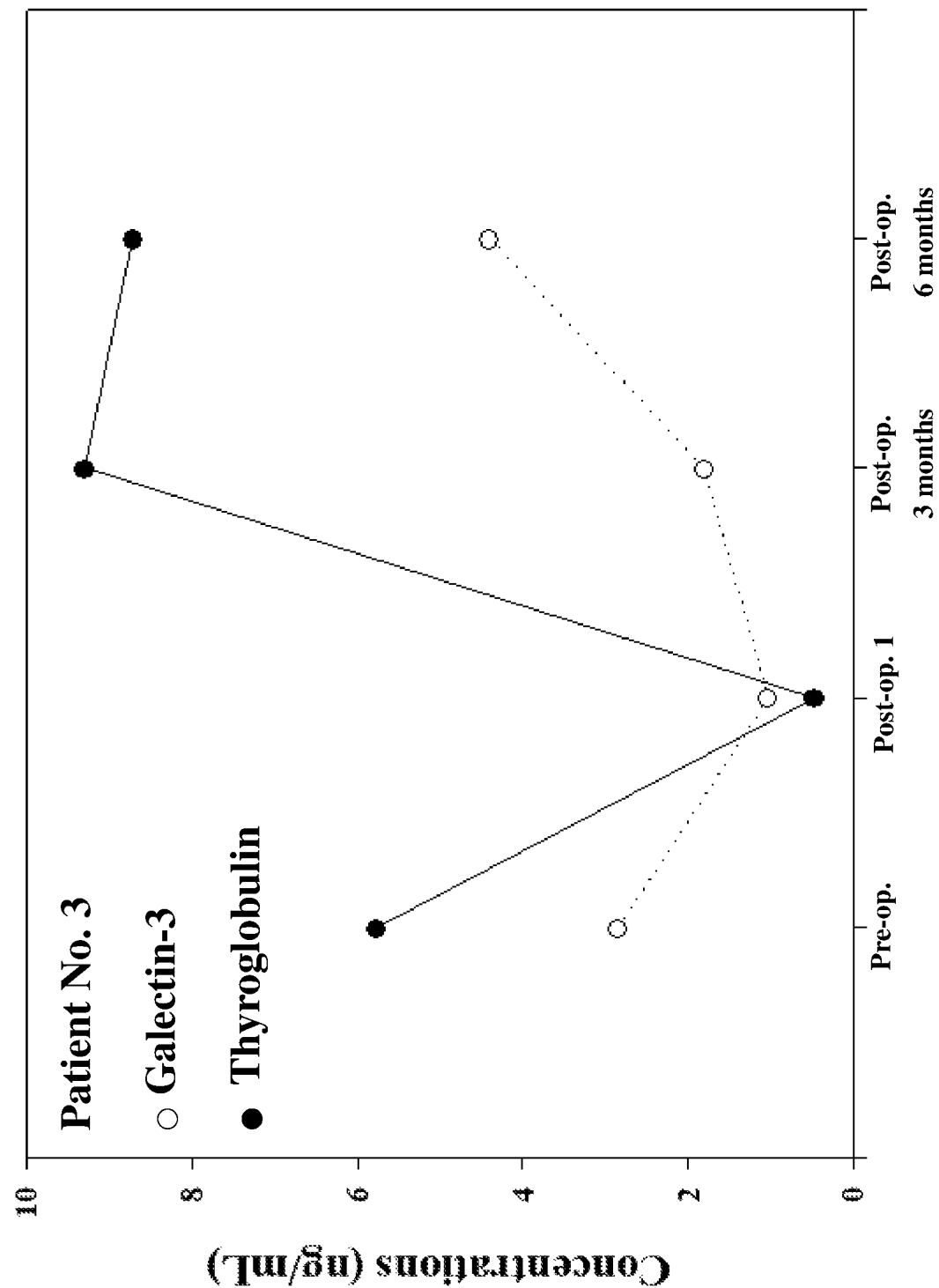
Figure 1D:
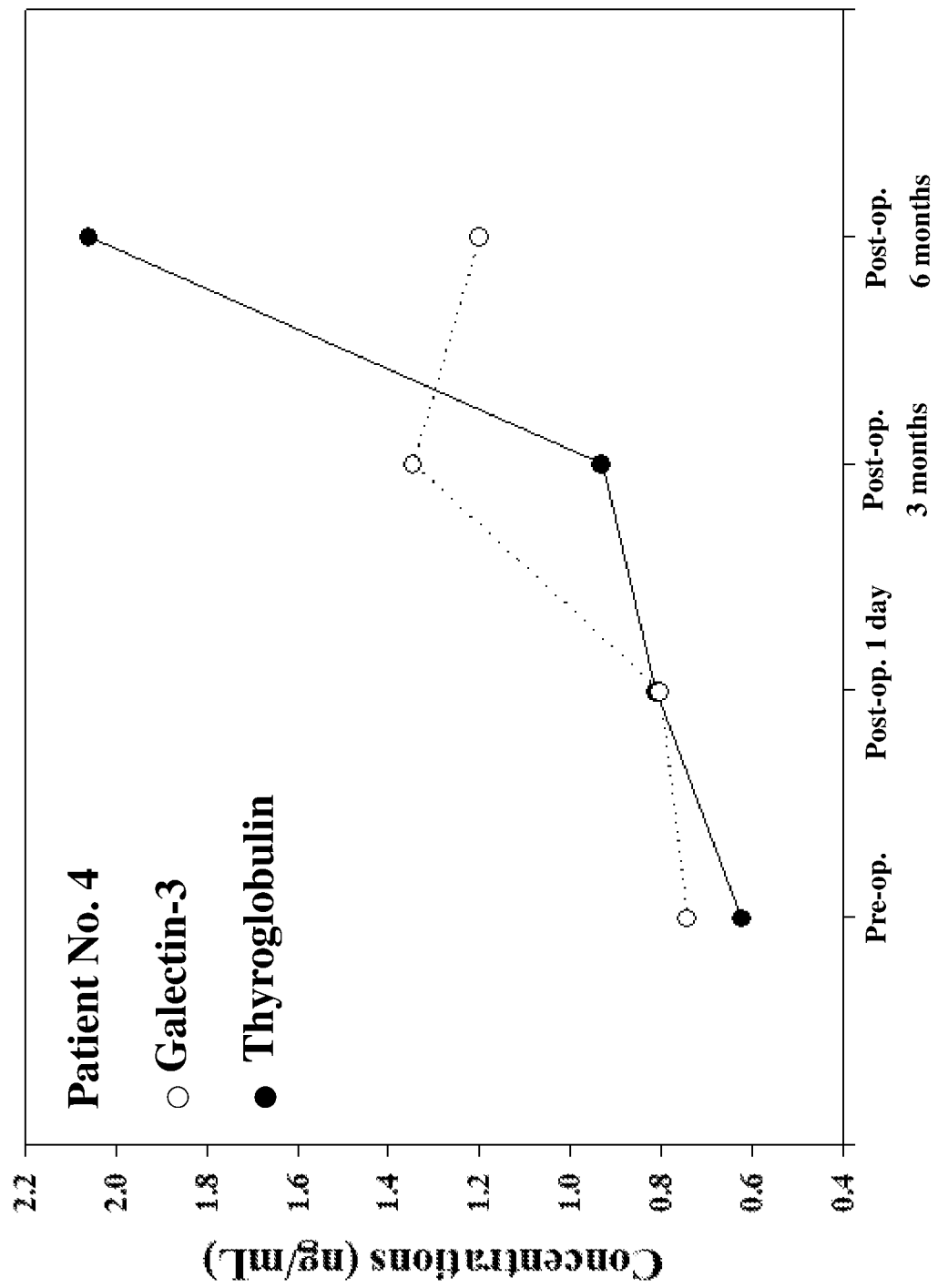
Figure 1E:
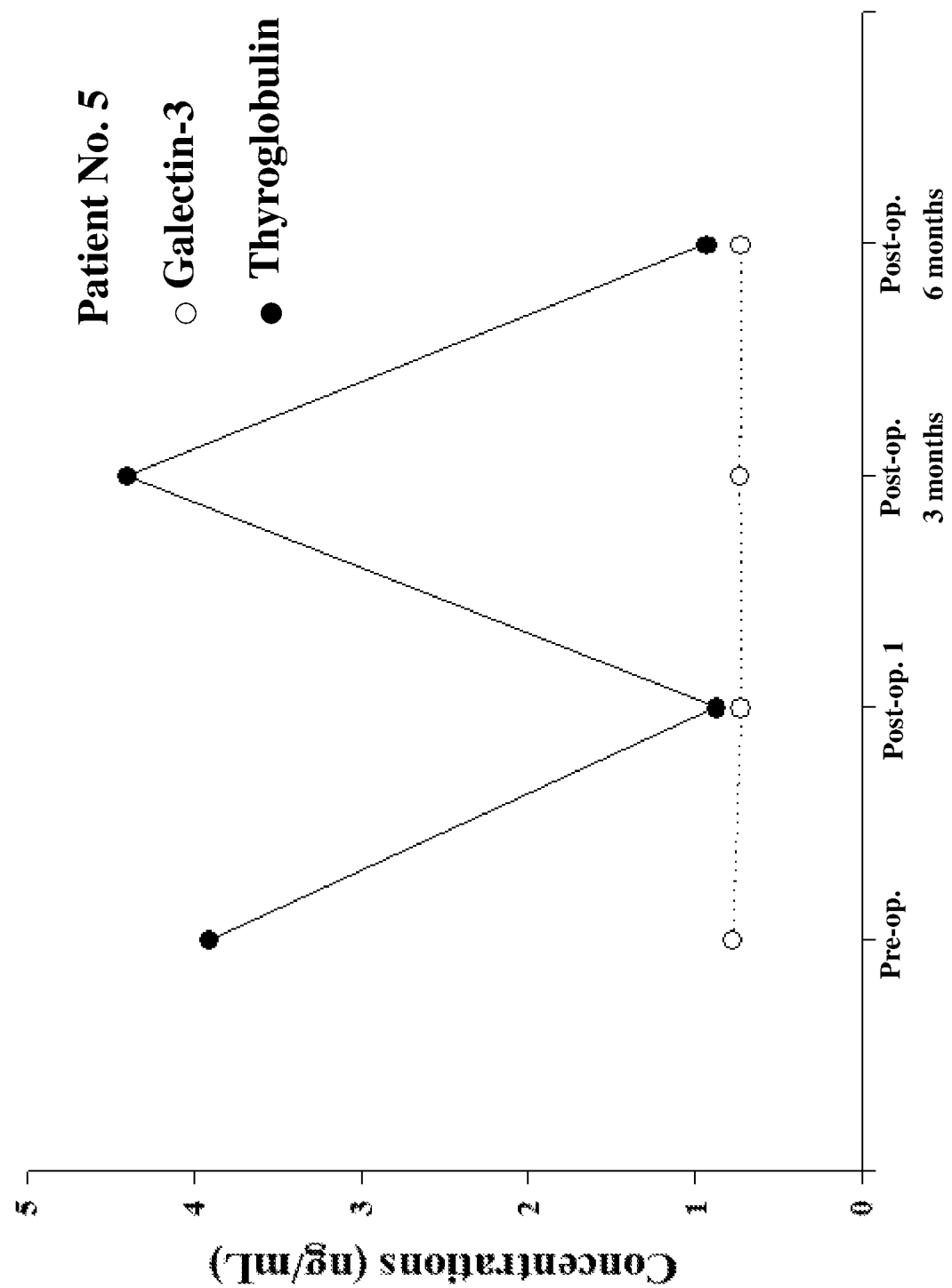
Figure 1F:
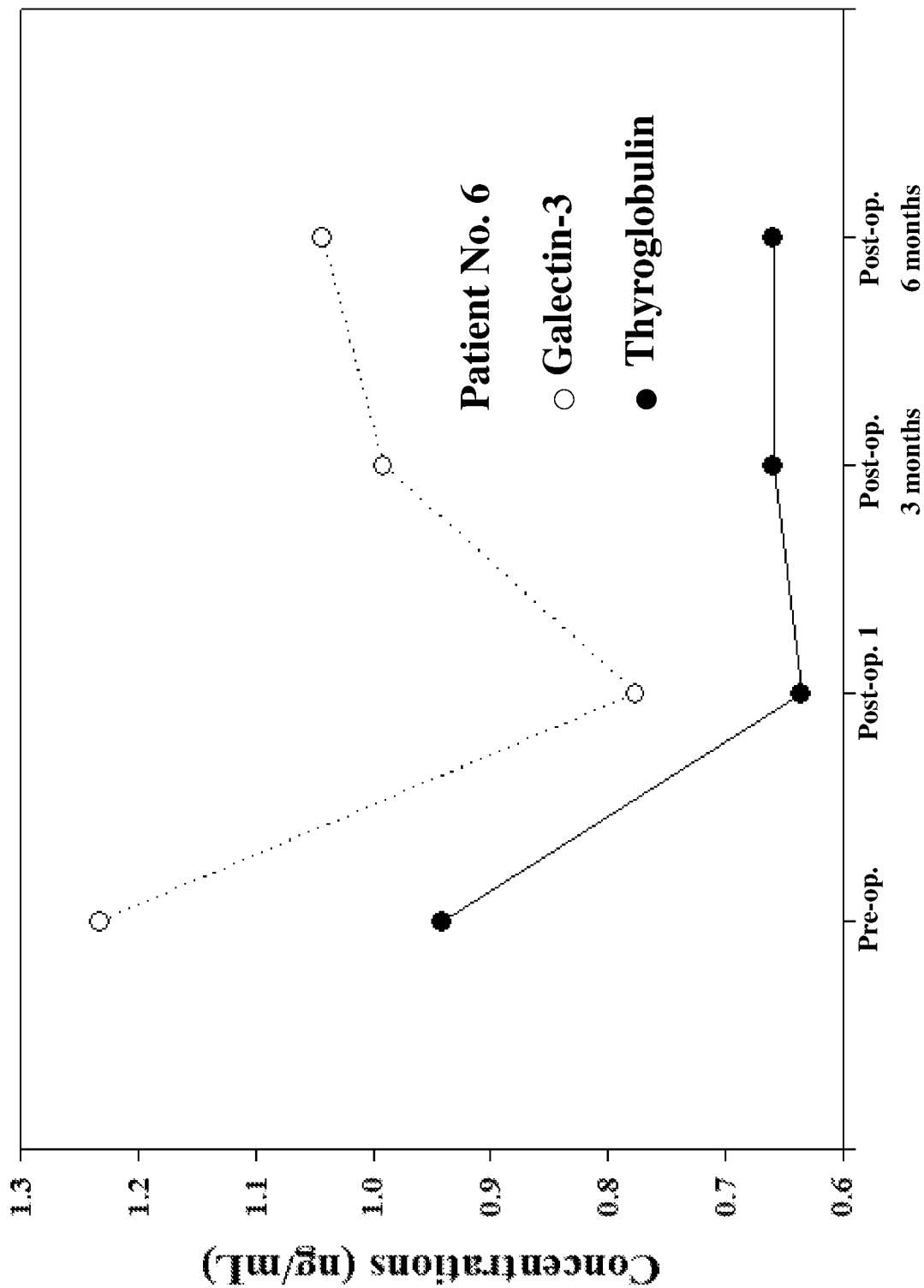
Figure 1G:
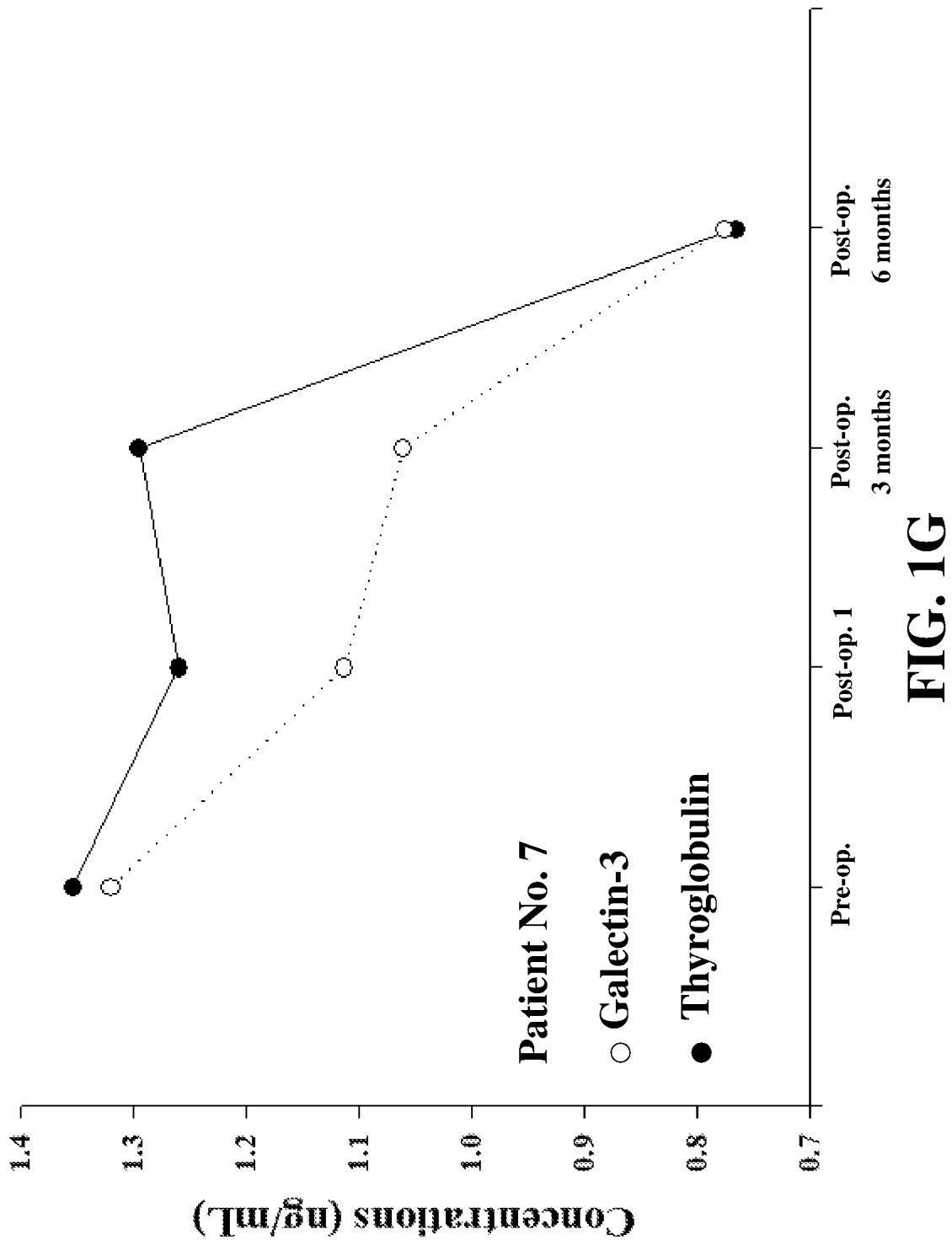
Figure 1H:
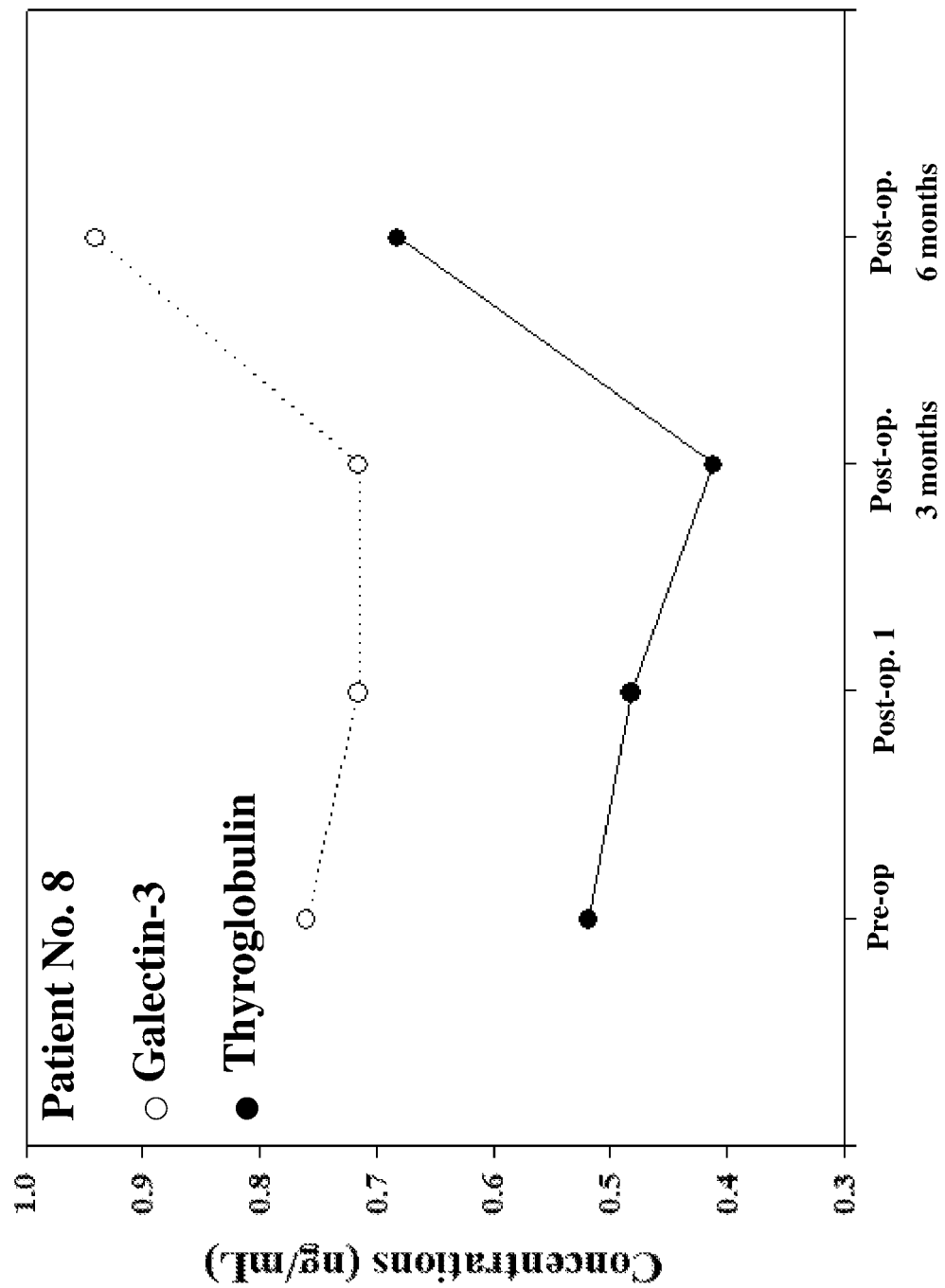
Figure 1I:
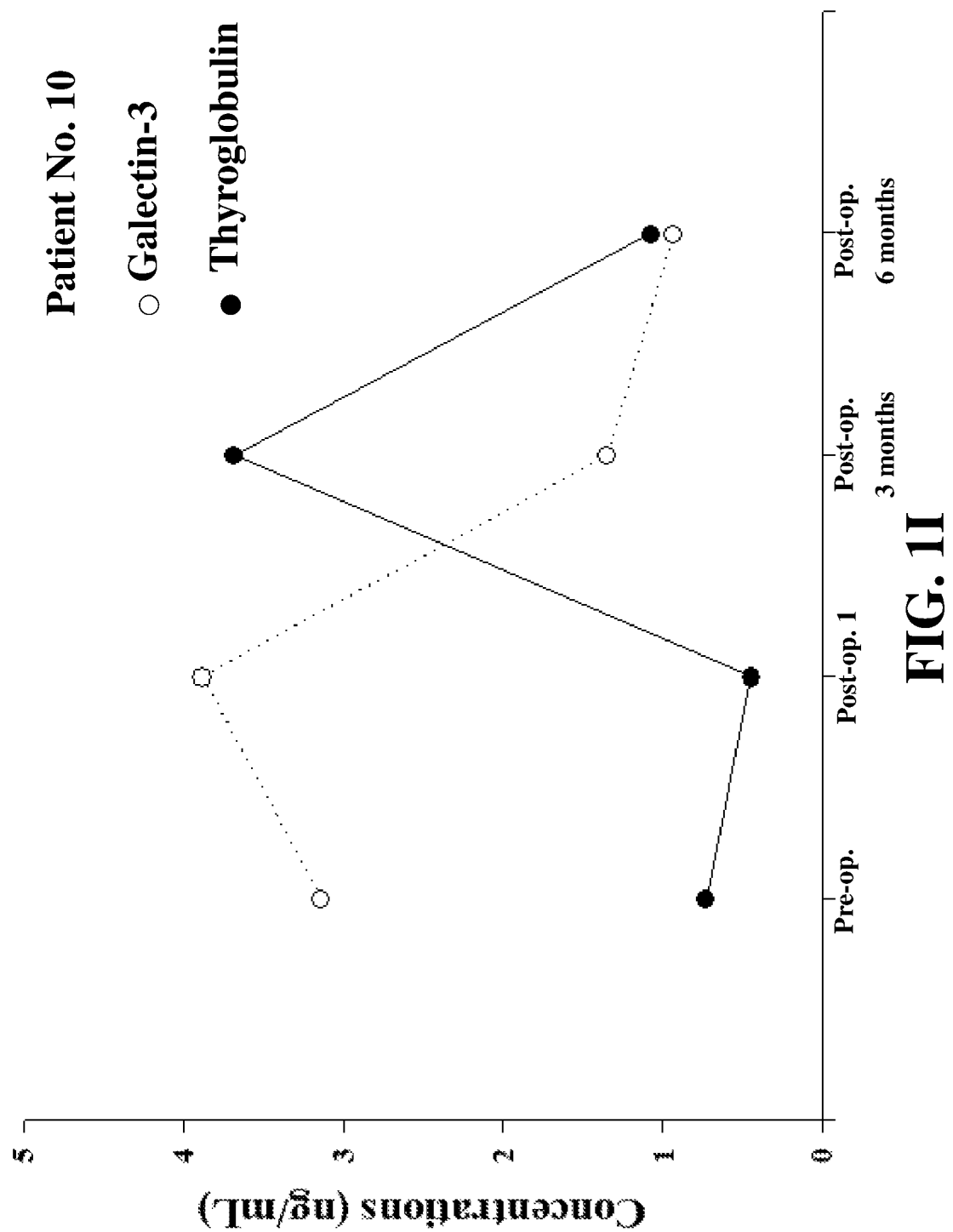
Figure 1J:
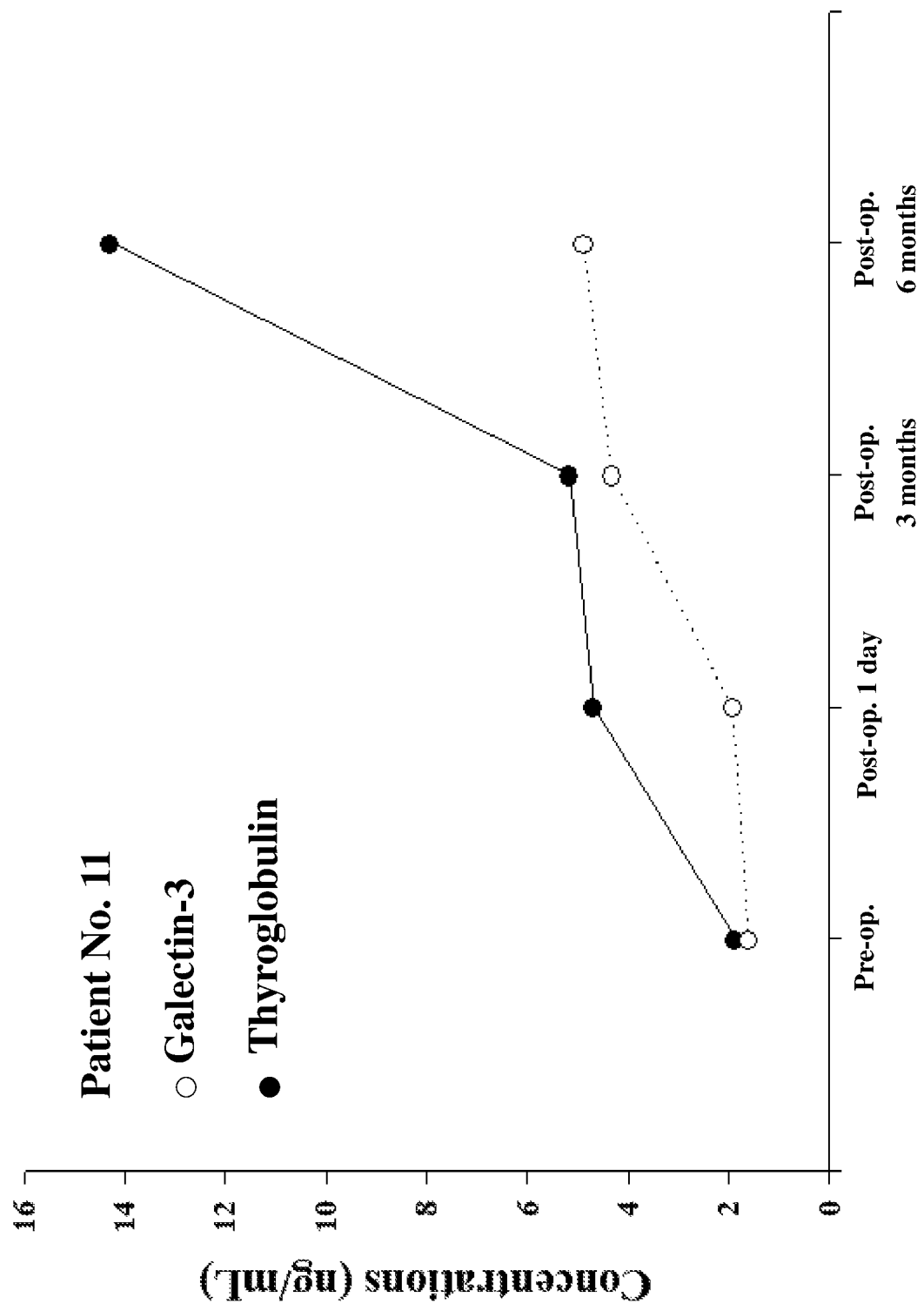
Figure 1K:
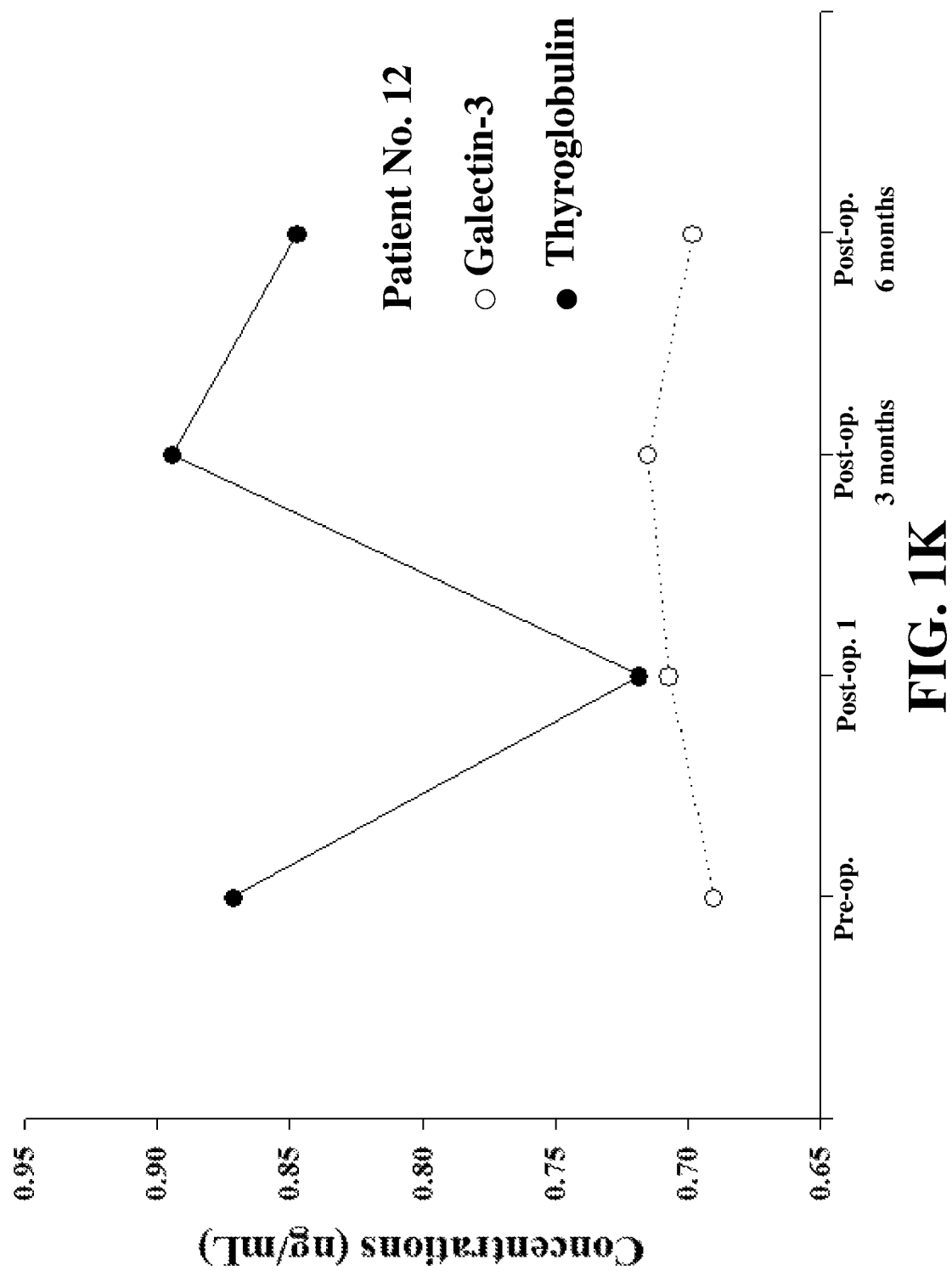
Figure 1L:
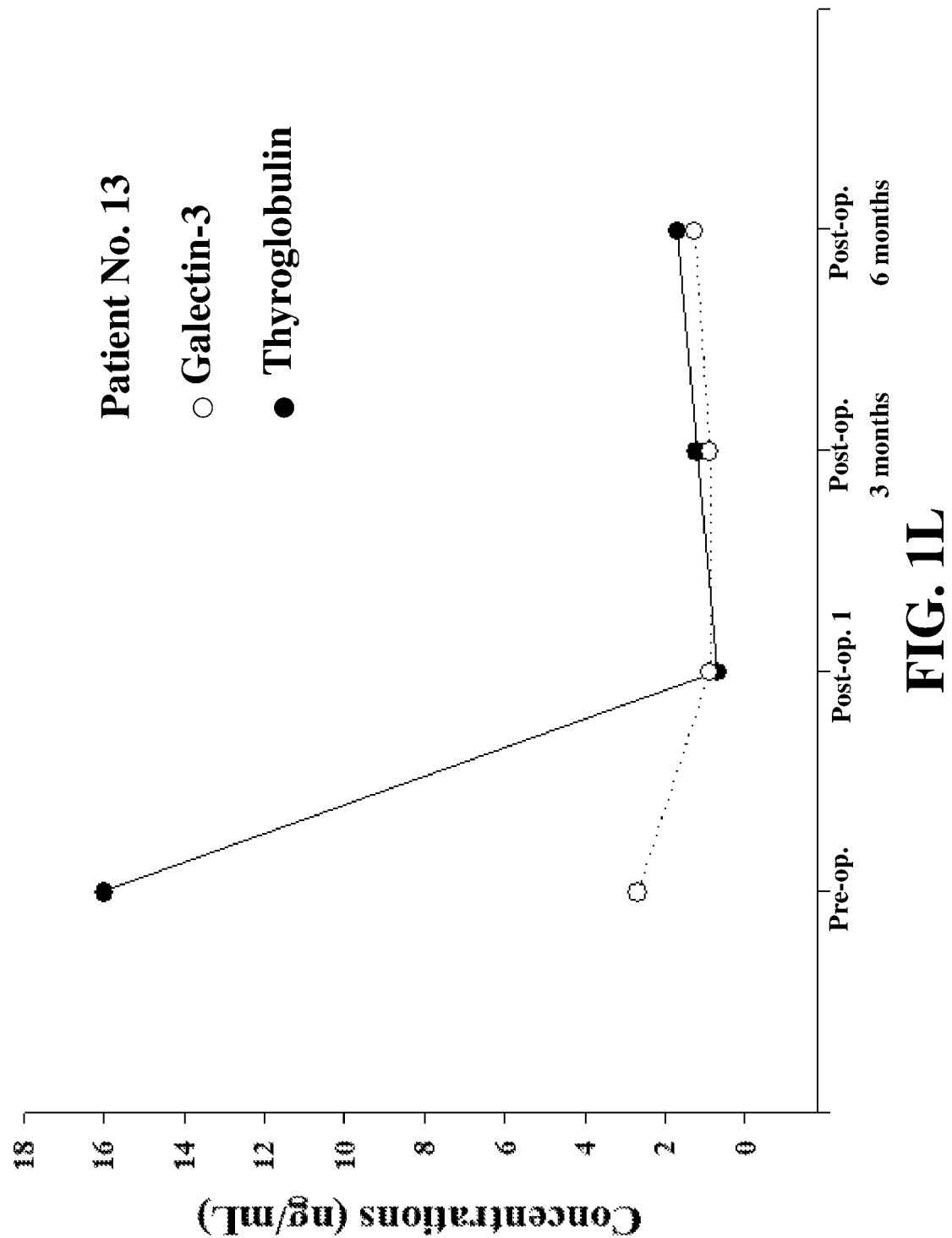
Figure 1M:
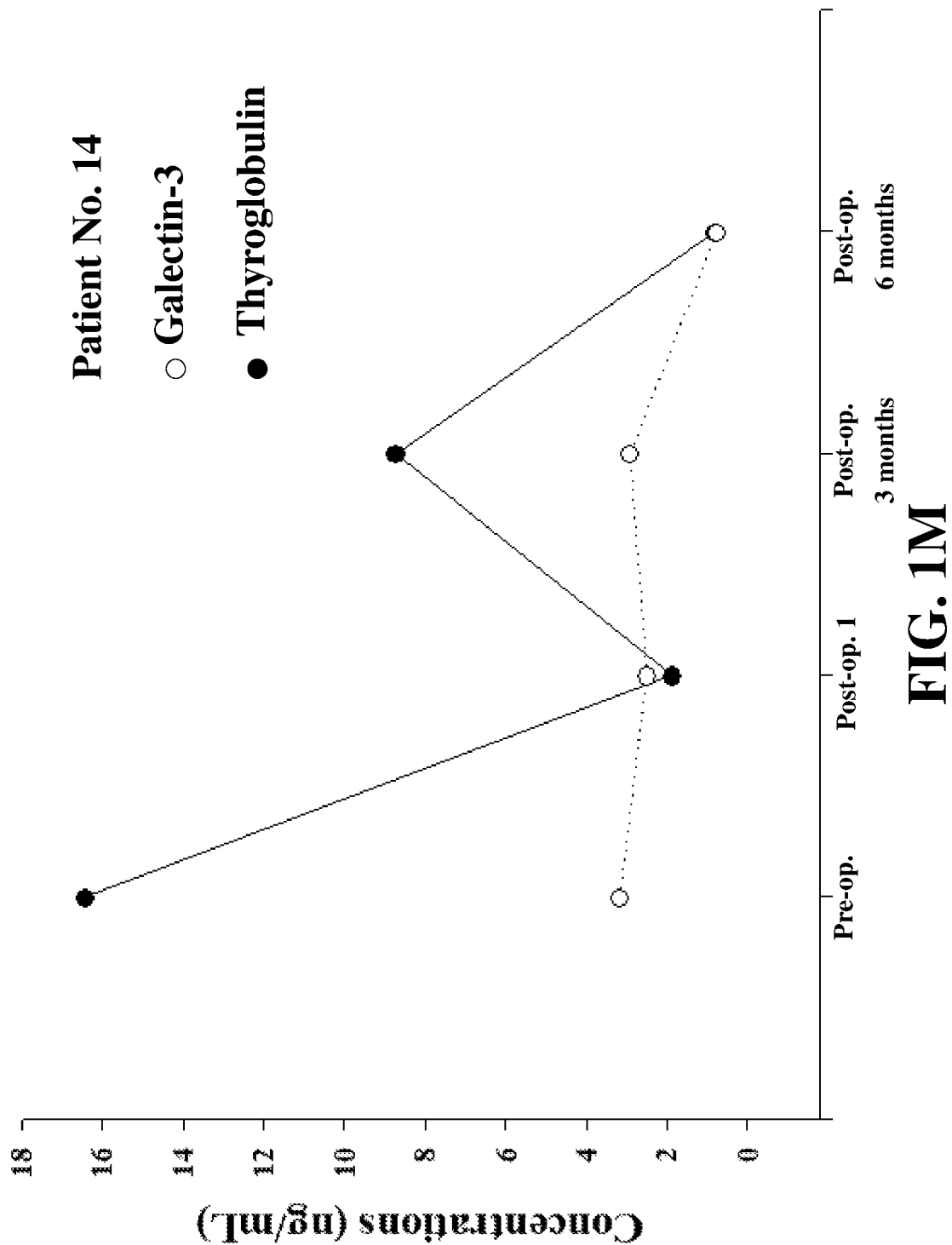

The present disclosure provides a method and biomarker of characterizing thyroid cancer in a subject by analyzing exosomes, and more particularly a sensitive and non-invasive method by analyzing urinary exosomal protein as the biomarker to determine prognosis in thyroid cancer patient. By the method of the present disclosure, the subject for determining prognosis of thyroid cancer is not required to withdraw thyroid hormone or receive rhTSH stimulation.

Currently, for patient with thyroid cancer who received thyroidectomy with ablative radioactive I-131 therapy, serum thyroglobulin is used as the cancer biomarker during follow-up. If thyroglobulin cannot be detected in the serum, patient is considered to have completed treatment, independently of the interference of anti-thyroglobulin antibody. Typically, serum thyroglobulin cannot be detected even under costly rhTSH stimulation in patient with biochemically complete treatment, making the serum thyroglobulin an insufficient biomarker for recurrence of thyroid cancer. The present disclosure discovers use of urinary exosomal thyroglobulin as a non-invasive, reproducible, convenient, serial, and accurate follow-up marker for patient with thyroid cancer. More specifically, peptide sequences are analyzed to quantify the levels of thyroglobulin in urine exosomes. Without the requirement for rhTSH, costs are reduced and patients can continue the use of thyroid hormone during cancer follow-up.

In the present disclosure, the exosome from biological sample obtained from a subject is analyzed to characterize the thyroid cancer. The exosome is nanovesicle secreted into extracellular environment from a variety of different cells such as but not limited to, cells that originate from, or are derived from, the ectoderm, endoderm, or mesoderm including any such cells that have undergone genetic, environmental, and/or any other variations or alterations (e.g., tumor cells or cells with genetic mutations). Exosomes are typically 40 nm to 100 nm in diameter and correspond to the intraluminal vesicles of endosomal multivesicular bodies. Exosomes can have, but not be limited to, a diameter of greater than about 10, 20, or 30 nm. They can have a diameter of about 30 nm to 1000 nm, about 30 nm to 800 nm, about 30 nm to 200 nm, or about 30 nm to 100 nm. In some embodiments, the exosomes can have, but not be limited to, a diameter of less than about 10,000 nm, 1000 nm, 800 nm, 500 nm, 200 nm, 100 nm or 50 nm. As used throughout, the term "about," when referring to a value or to an amount is meant to encompass variations in some embodiments ±10% from the specified amount, as such variations are appropriate.

Exosomes secreted by cells transfer molecular messages between cells and are used as biological markers of cancer, for the diagnosis and prognosis of malignant tumors. Exosomal proteins can influence cellular signaling, inflammation, immunity. In addition, inflammatory exosomal proteins contribute to various patho-physiological processes in cellular behavior. Exosomes can be collected from the biological sample from a subject, such as serum, tissue fluid, and urine for characterizing diseases.

The biological sample obtained from the subject may be any bodily fluid. For example, the biological sample can be peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen (including prostatic fluid), Cowper's fluid or pre-ejaculatory fluid, female ejaculate, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates or other lavage fluids. A biological sample may also include the blastocyl cavity, umbilical cord blood, or maternal circulation which may be of fetal or maternal origin. The biological sample may also be a tissue sample or biopsy, from which exosomes may be obtained.

Exosomes can be directly assayed from the biological samples, such that the level of exosomes is determined or the biomarker in the exosomes is determined without prior isolation, purification, or concentration of the exosomes. Alternatively, exosomes may be isolated, purified, or concentrated from a sample prior to analysis.

An enriched population of exosomes can be obtained from a biological sample. For example, exosomes may be concentrated or isolated from a biological sample using size exclusion chromatography, density gradient centrifugation, differential centrifugation, nanomembrane ultrafiltration, immunoabsorbent capture, affinity purification, microfluidic separation, or combinations thereof.

Size exclusion chromatography, such as gel permeation columns, centrifugation or density gradient centrifugation, and filtration methods can be used. For example, exosomes can be isolated by differential centrifugation, anion exchange and/or gel permeation chromatography, sucrose density gradients, organelle electrophoresis, magnetic activated cell sorting (MACS), or with a nanomembrane ultrafiltration concentrator. Various combinations of isolation or concentration methods can be used.

The isolated exosomes are subjected to analysis for biomarkers in this disclosure for prognosis of thyroid cancer or evaluation of the therapy of thyroid cancer. Accordingly, exemplary embodiments of present disclosure provide methods for detecting the presence of, or abundance levels of thyroglobulin in the isolated exosomes from a biological sample. Thyroglobulin can be analyzed by ELISA, mass spectrometry or flow cytometry. Proteomic analysis of exosomes may also be carried out on exosomes by immunocytochemical staining, Western blotting, electrophoresis, chromatography or X-ray crystallography in accordance with procedures well known in the art.

In other embodiments, the protein bio-signatures of exosomes may be analyzed using 2D differential gel electrophoresis, or with liquid chromatography mass spectrometry. Exosomes may be subjected to activity-based protein profiling. In other embodiments, exosomes may be profiled using nanospray liquid chromatography-tandem mass spectrometry. In another embodiment, the exosomes may be profiled using tandem mass spectrometry (MS) such as liquid chromatography/MS/MS (LC-MS/MS) using for example a LTQ and LTQ-FT ion trap mass spectrometer. Protein identification can be determined and relative quantitation can be assessed by comparing spectral counts.

All terms including descriptive or technical terms which are used herein should be construed as having meanings that are obvious to one of ordinary skill in the art. However, the terms may have different meanings according to an intention of one of ordinary skill in the art, case precedents, or the appearance of new technologies. Also, some terms may be arbitrarily selected by the applicant, and in this case, the meaning of the selected terms will be described in detail in the detailed descriptions of the present disclosure. Thus, the terms used herein have to be defined based on the meaning of the terms together with the descriptions throughout the specification.

Also, when a part "includes" or "comprises" a component or a step, unless there is a particular description contrary thereto, the part can further include other components or other steps, not excluding the others.

It is further noted that, as used in this specification, the singular forms "a," "an," and "the" include plural referents unless expressly and unequivocally limited to one referent. The term "or" is used interchangeably with the term "and/or" unless the context clearly indicates otherwise.

The term "to characterize" in a subject or individual may include, but is not limited to, the diagnosis of a disease or condition, the prognosis of a disease or condition, the determination of a disease stage or a condition stage, monitoring for a recurrence of cancer, a drug efficacy, a physiological condition, organ distress or organ rejection, disease or condition progression, therapy-related association to a disease or condition, or a specific physiological or biological state.

The term "peptide" used herein means a short chain containing more than one amino acid monomers, in which the more than one amino acid monomers are linked to each other by amide bonds. It must be noted that the amino acid monomers used in the peptide of the present disclosure are not limited to natural amino acids, and the amino acid sequence of the peptide can also include unnatural amino acids, compounds with similar structure, or the deficiency of amino acids.

The following examples are used to exemplify the present disclosure. A person of ordinary skill in the art can conceive the other advantages of the present disclosure, based on the specification of the present disclosure. The present disclosure can also be implemented or applied as described in different examples. It is possible to modify and/or alter the above examples for carrying out this disclosure without contravening its spirit and scope, for different aspects and applications.

EXAMPLE

Exemplary embodiments of the present disclosure are further described in the following examples, which do not limit the scope of the present disclosure.

The following examples describe the steps to analyze the urinary exosomal proteins from exosomes isolated from urine sample as the early prognostic biological markers.

Thirteen patients with newly diagnosed papillary or follicular thyroid cancer were followed-up for six months. All thirteen patients received total thyroidectomy after surgical assessment, and nine patients received radioactive I-131 ablation at approximately four weeks after operation.

Example 1 Patient Assessment

All patients received comprehensive pre-operative and post-operative assessment of thyroid function, including serum thyroglobulin and anti-thyroglobulin antibody levels, surgical pathology findings with staging of cancer determined according to the TNM classification of malignant tumors, in addition to the basic demographic information. Thyroglobulin levels were determined using IMMULITE 2000 Thyroglobulin, a solid-phase, chemiluminescent immunometric assay. Its analytical sensitivity is 0.2 ng/mL (Siemens, Erlangen, Germany) Level of anti-thyroglobulin antibody was determined with ARCHITECT Anti-Tg assay, which is a two-step immunoassay for quantitative determination of thyroglobulin auto-antibodies in human serum. Its sensitivity is ≤1.0 IU/mL (Abbott Laboratories, Chicago, IL, USA). Results from the assessment were shown in the following Table 1.

TABLE 1

| Patient No. | Gender | Age | Date of OP. | Date of radioactive I-131 | I-131 Ablation Dose | FT4 Post-OP. | hsTSH Post-OP. | Tg Pre-OP. | Tg Post-OP. 6 months | Anti-Tg Ab Post-OP. 6 months | Pathology |
|---|---|---|---|---|---|---|---|---|---|---|---|
| 1 | F | 49 | 2016 Aug. 20 | 2016 Sep. 29 | 30 mCi | 0.981 | 0.212 | 93.6 | <0.2 | <3.0 | PTC with minimally extra-thyroid soft tissue involvement, TNM: T3N0M0 |
| 2 | F | 58 | 2016 Sep. 8 | NA | NA | 1.13 | 2.12 | NA | <0.2 | 50.4 | PTC with clear surgical margin, TNM: T1aN0M0 |
| 3 | F | 57 | 2016 Sep. 12 | 2016 Oct. 14 | 30 mCi | 1.24 | 2.96 | NA | <0.2 | <3.0 | PTC with minimally extra-thyroid soft tissue involvement, TNM: T3N0M0 |
| 4 | F | 42 | 2016 Sep. 12 | 2016 Oct. 14 | 30 mCi | 1.24 | 0.611 | <0.2 | <0.2 | 6.03 | PTC with metastasis of level IV lymph nodes, TNM: T1bN1aM0 |

TABLE 1-continued

| Patient No. | Gender | Age | Date of OP. | Date of radioactive I-131 | I-131 Ablation Dose | FT4 Post-OP. | hsTSH Post-OP. | Tg Pre-OP. | Tg Post-OP. 6 months | Anti-Tg Ab Post-OP. 6 months | Pathology |
|---|---|---|---|---|---|---|---|---|---|---|---|
| 5 | F | 34 | 2016 Oct. 15 | 2016 Nov. 18 | 30 mCi | 1.07 | 11.3 | NA | <0.2 | <3.0 | PTC with minimally capsular invasion, TNM: T3N0M0 |
| 6 | F | 52 | 2016 Nov. 19 | NA | NA | 1.01 | 0.249 | NA | 3.80 | 4.47 | PTC with limited in the thyroid, TNM: T1aN0M0 |
| 7 | F | 43 | 2016 Dec. 8 | 2017 Jan. 20 | 30 mCi | 1.58 | 1.19 | NA | <0.2 | 6.08 | PTC with limited in the thyroid, TNM: T1bN0M0 |
| 8 | M | 48 | 2016 Dec. 5 | 2017 Jan. 12 | 30 mCi | 1.10 | 4.05 | NA | <0.2 | 6.95 | FTC with minimal capsular invasion and focal lymph-vascular invasion, TNM: T1bN0M0 |
| 10 | F | 54 | 2017 Feb. 6 | NA | NA | 0.841 | 3.04 | NA | 16.8 | <3.0 | Hurthle cell adenoma |
| 11 | M | 41 | 2017 Apr. 22 | 2017 Jul. 20 | 150 mCi | 2.23 | 0.059 | NA | 27.4 | 3.46 | Papillary carcinoma, with minimal extra-thyroid extension, TNM: T3N0M1 (lung) |
| 12 | F | 59 | 2017 Apr. 10 | NA | NA | 1.27 | 0.960 | NA | 9.14 | <3.0 | Papillary microcarcinoma, TNM: T1aN0M0 |
| 13 | F | 45 | 2017 Mar. 18 | 2017 Apr. 21 | 30 mCi | 0.963 | 118 | NA | <0.2 | <3.0 | PTC (multifoci), TNM: T3N0M0 |
| 14 | F | 41 | 2017 May 1 | 2017 Jul. 26 | 125 mCi | 1.32 | 0.998 | 1.34 | <0.2 | 119.52 | PTC, TNM: T1bN1aM0 |

*F: Female; M: Male; OP: operation; FT4: free T4 (normal range: 0.89-1.76 ng/dL); Tg: thyroglobulin (normal range: <55.0 ng/mL); hsTSH: high sensitivity TSH (normal range: 0.4-4.0 mIU/mL); Anti-Tg Ab: anti-thyroglobulin antibody (normal range: <14.4 IU/mL); PTC: papillary thyroid carcinoma; TNM staging (according to AJCC, American Joint Committee on Cancer, 7th edition); NA: Not Available Table 1 lists the results of patient assessments, including basic demographic information, pre-operative and post-operative assessment of thyroid function, including serum thyroglobulin and anti-thyroglobulin antibody levels, surgical pathology findings with staging of cancer determined according to the TNM classification of malignant tumors.

Example 2 Urine Sample Collection

Urine samples were collected from patients before operation, immediately after operation, post-operatively at three and six months for a total of 4 collections per patient. Urine samples from the patients were collected for urinary exosome precipitation. Specifically, 200 mL of fresh human urinary sample was collected for each patient. These samples were centrifuged at 3000×g for 15 min at 4° C. to remove cells and cell debris, and then centrifuged at 10,000×g for 30 min at 4° C. to remove microvesicles.

Amicon® Ultra 15-centrifugal filters, 100K (Millipore, Billerica, MA, USA) were used to concentrate the 200 mL urinary samples to 5 mL to 10 mL. Urinary exosomes were isolated using ExoQuick-TC (System Biosceinces, Palo Alto, CA, USA). Supernatants were transferred to new tubes, cOmplete™, EDTA-free Protease Inhibitor Cocktail (Roche, Basel, Switzerland) was added, and samples were stored at −80° C. Exosome pellets were resuspended in lysis buffer (7 M urea, 2 M thiourea, 4% CHAPS). Exosome protein samples thus prepared were frozen at −80° C. until multiple reaction monitor (MRM) analysis.

Example 3 Tryptic Digestion of Exosome Protein

Urinary exosome samples were precipitated with three volumes of cold methanol at −20° C., followed by centrifugation at 10,000×g for 10 min. The precipitated pellet was then suspended in lysis buffer (4 M urea, 25 mM ammonium bicarbonate, pH 8.5). The denatured samples were reduced with 200 mM dithiothreitol at ambient temperature for 1 h and then alkylated with 200 mM iodoacetamide in the dark for 1 h. The remaining iodoacetamide was quenched by the addition of 200 mM DTT and incubated at ambient temperature for 20 mM Modified sequencing-grade trypsin (Promega, Madison, WI, USA) was added to samples. Digestion was carried out for 16 h at 37° C.

Example 4 MRM Q1/Q3 Ion Pair Selection Using Direct Infusion

Galectin-3 is used for comparison to confirm the trends in thyroglobulin levels. Galectin-3 modulates cell growth via galactosidase-binding protein, which is correlated with occurrence and metastasis of papillary thyroid cancer.

Peptide sequences of thyroglobulin and galectin-3 are available from Peptide Atlas and UniProt, and shown in Table 2 below.

TABLE 2

Standard peptide sequence for representative protein

| Standard peptide | Sequence | Molecular weight (Dalton) |
|---|---|---|
| Thyroglobulin | FLAVQSVISGR (SEQ ID NO. 1) | 1176.38 |
| Galectin-3 | IALDFQR (SEQ ID NO. 2) | 862.00 |

Standard peptides were synthesized by Mission Biotech, Ltd. (Taipei, Taiwan). The synthetic peptides were dried and precipitated with ether. Peptides were purified by reverse-phase high-performance liquid chromatography while monitoring peptide elution at 230 nm. Synthetic standard peptides were diluted to 2 µg/mL in 0.1% formic acid for infusion at a flow rate of 10 µL/min using a syringe pump. The infused peptide solutions were analyzed by electrospray ionization using an AB SCIEX QTRAP 5500 mass spectrometer (Framingham, MA, USA) equipped with the TurboV source and controlled by Analyst software. Mass spectrometry analysis was conducted in positive ion mode with the ion spray voltage set to 5500 V. The source temperature was set to 550° C. Additional parameters were nebulizer and drying gas flow at 60 and 45 psi, respectively. Analyst software was used to generate a list of all possible b- and y-series fragment ions for both 2+ and 3+ precursor ion-charge state spanning m/z range from 100 to 1000. MRM scans for optimization of MRM Q1/Q3 ion pairs were conducted with both Q1 and Q3 set to unit resolution (0.7 Da full width at half maximum), while the collision energy (CE) was ramped from 5 to 55 V in 1-V increments, with dwell time of 150 ms for each transition. From this data, the four transitions that produced the strongest signals were selected on a per-peptide basis. Next, the three transitions producing the most abundant signals free of signal interferences were selected from these four transitions.

Example 5 LC-MRM/MS Analysis of Urinary Exosome Digests

An Agilent 1260 Infinity HPLC system (Agilent Technologies, Santa Clara, CA, USA) was used to directly inject 10 µL of urine digest samples onto a reverse-phase analytical column (100×2.1 mm i.d., 2.7 µm, Agilent Poroshell 120 EC-C18) that was maintained at ambient temperature. Samples were separated using a 300 µL/min flow rate and gradient of 3% to 90% of mobile phase B over a total run time of 30 min. Mobile phase A consisted of 0.1% v/v formic acid, while mobile phase B consisted of ACN/0.1% formic acid. The gradient method is composed of multiple linear gradients as follows (time: % B): 0.1 min, 10% B; 3.5 min, 11% B; 6.5 min, 20% B; 7 min, 21% B; 7.5 min, 22% B; 12.5 min, 22.5% B; 17 min, 25% B; 20 min, 30% B; 22.5 min, 42% B; 23.5 min, 90% B; 27 min, 3% B; 30 min, 3% B. An AB SCIEX QTRAP 5500 with a TurboV ionization source, controlled by Analyst software, was used for all LC-MRM/MS sample analyses. All acquisition methods used the following parameters: 5500 V ion spray voltage, nebulizer and drying gas flow of 60 and 45 psi, respectively, source temperature of 550° C., and Q1 and Q3 set to unit resolution (0.7 full width at half maximum).

MRM acquisition methods were initially composed of four ion pairs per peptide during determination of high-signal producing interference-free transitions and LC method development. The final analytical method was composed of one verified quantifier ion pair per peptide, and is a high-throughput, rapid 30-min method that has been evaluated for common urine interferences. However, urine analysis of the samples was performed with acquisition methods containing three verified ion-pair transitions per target peptide to ensure the detection of any minor sample-specific signals. MRM acquisition methods were constructed using fragment ion-specific tuned CE voltages and retention time constraints.

Example 6 MRM Data Analysis of Peptide Targets in Urinary Exosome Digests

All MRM data were processed using AB SCIEX Analyst software (version 1.5) with the Integrator algorithm for peak integration set to default values. All integrated peaks were manually inspected to ensure correct peak detection and accurate integration. Linear regression of all calibration curves was performed using a standard $1/x^2$ (x=concentration) weighting option to aid in covering a wide dynamic range. The concentration of each peptide target was calculated based on the observed response and experimentally determined linear regression equation from the standard curve. The calculated concentration is in µM and converted to ng/mL by taking into account the weight of the entire processed protein using the formula (ng/mL)=(µM)× (molecular weight in Dalton).

Urinary peptide biomarkers concentrations of the thirteen patients were tabulated in the following Table 3, and the trends for each patient depicted in FIG. 1A to FIG. 1M.

TABLE 3

Peptide concentrations (ng/mL) of thyroglobulin and galectin-3 in urinary exosomal proteins

| Patient No. | Peptide | Pre-op. | Post-op. 1 day | Post-op. 3 months | Post-op. 6 months |
|---|---|---|---|---|---|
| 1 | Thyroglobulin | 0.35291 | 0.58819 | 7.06 | 3.06 |
|   | Galectin-3 | 1.55 | 2.16 | 2.59 | 3.62 |
| 2 | Thyroglobulin | 1.88 | 7.65 | 3.53 | 0.58819 |
|   | Galectin-3 | 1.9 | 3.88 | 1.47 | 0.6034 |
| 3 | Thyroglobulin | 5.76 | 0.47055 | 9.29 | 8.71 |
|   | Galectin-3 | 2.84 | 1.03 | 1.81 | 4.4 |
| 4 | Thyroglobulin | 0.623 | 0.812 | 0.929 | 2.059 |
|   | Galectin-3 | 0.741 | 0.802 | 1.345 | 1.198 |
| 5 | Thyroglobulin | 3.906 | 0.871 | 4.400 | 0.929 |
|   | Galectin-3 | 0.776 | 0.724 | 0.733 | 0.724 |
| 6 | Thyroglobulin | 0.941 | 0.635 | 0.659 | 0.659 |
|   | Galectin-3 | 1.233 | 0.776 | 0.991 | 1.043 |
| 7 | Thyroglobulin | 1.353 | 1.259 | 1.294 | 0.765 |
|   | Galectin-3 | 1.319 | 1.112 | 1.060 | 0.776 |
| 8 | Thyroglobulin | 0.518 | 0.482 | 0.412 | 0.682 |
|   | Galectin-3 | 0.759 | 0.715 | 0.715 | 0.940 |
| 10 | Thyroglobulin | 0.729 | 0.447 | 3.682 | 1.071 |
|   | Galectin-3 | 3.138 | 3.879 | 1.345 | 0.931 |
| 11 | Thyroglobulin | 1.870 | 4.682 | 5.164 | 14.281 |
|   | Galectin-3 | 1.603 | 1.922 | 4.319 | 4.879 |
| 12 | Thyroglobulin | 0.871 | 0.718 | 0.894 | 0.847 |
|   | Galectin-3 | 0.690 | 0.707 | 0.715 | 0.698 |
| 13 | Thyroglobulin | 15.999 | 0.694 | 1.200 | 1.694 |
|   | Galectin-3 | 2.672 | 0.879 | 0.888 | 1.259 |
| 14 | Thyroglobulin | 16.399 | 1.859 | 8.717 | 0.788 |
|   | Galectin-3 | 3.172 | 2.500 | 2.914 | 0.759 |

These data showed that while serum thyroglobulin was not detected with chemiluminescent immunometric assay at high sensitivity (0.2 ng/ml), urinary exosomal thyroglobulin could be detected by peptide sequencing. Particularly, serum thyroglobulin was not detected in patients 1, 3, 4 and 8 after radioactive I-131 ablation; however, urinary exosomal thyroglobulin showed an increasing trend, suggesting possible recurrence of thyroid cancer. In patients 10, 11 and 12 from whom serum thyroglobulin could be detected, urinary exosomal thyroglobulin levels also correlate well with an increasing trend.

Figure 2:
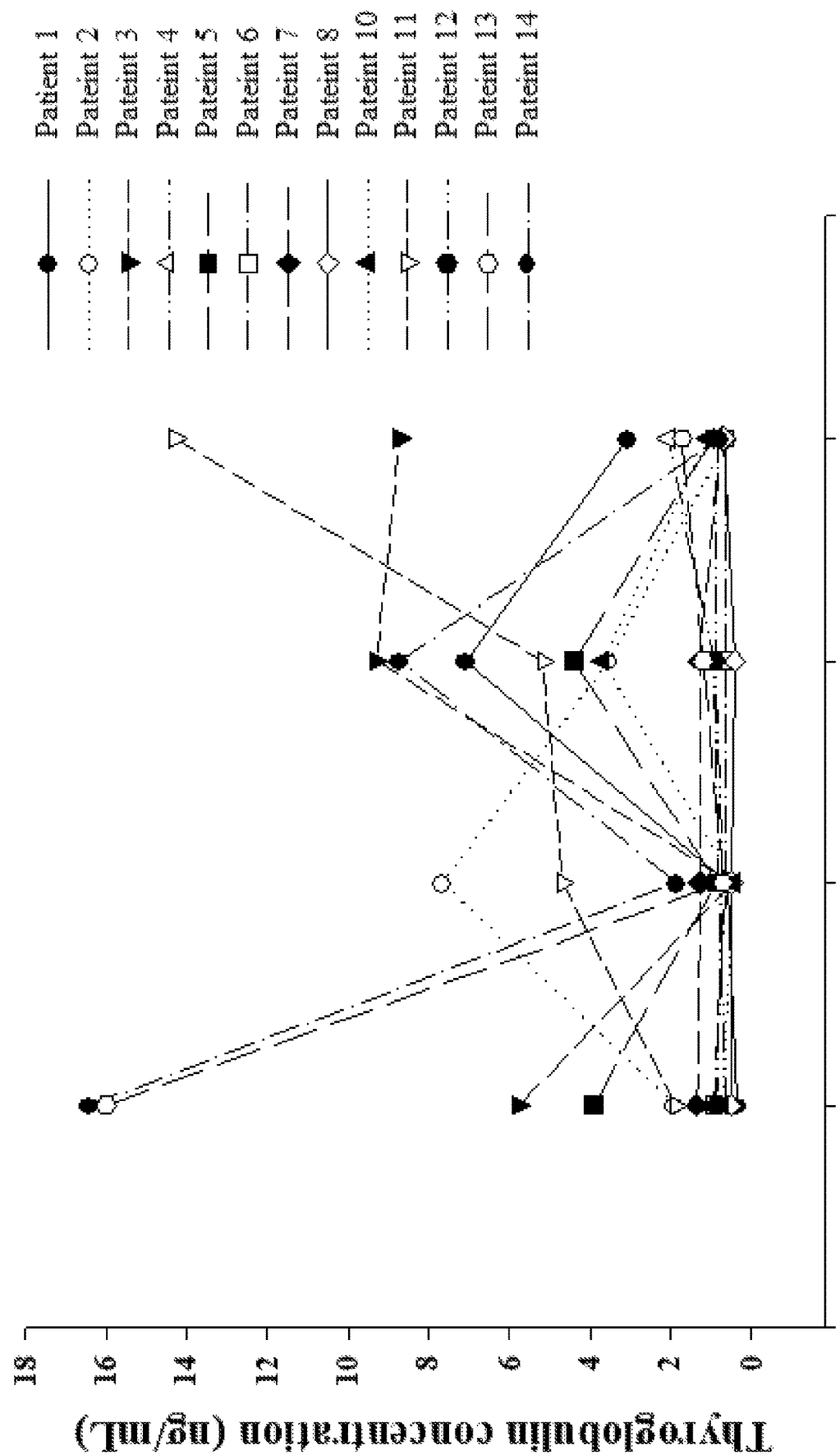
FIG. 2 shows the trends urinary exosomal protein levels before and after operation in patients receiving total thyroidectomy and radio-active iodine ablation.

In addition, pre-operative and post-operative serial changes of urinary exosomal thyroglobulin in patients receiving total thyroidectomy and radio-active iodine ablation were revealed in FIG. 2.

As shown in FIG. 2, the urinary exosomal thyroglobulin showed trends of elevation in patients 1, 3, 4 and 8 who were papillary thyroid cancer with soft tissue involvement, or with metastasis of level IV lymph nodes, or follicular thyroid cancer with lymph-vascular invasion. However, serum thyroglobulin in these patients cannot be detected after ablative therapy in the follow-up six months post operation.

Compared with serum thyroglobulin, urinary exosomal thyroglobulin using in the method of the present disclosure is a pro-inflammatory predictor and a more sensitive biomarker of thyroid cancer recurrence for the patient who had been subjected to thyroidectomy. The increasing tendency of urinary exosomal thyroglobulin in such patient suggest that it can be used as a better substitute for undetectable serum thyroglobulin in predicting the recurrence, and act as a sensitive and early biomarker in the monitoring of thyroid cancer patients.

What is claimed is:

1. A method of prognosis of thyroid cancer in a subject in need thereof, comprising:
   obtaining an exosome from the subject who had received a therapy of thyroid cancer, wherein the exosome is isolated from urine;
   detecting a trend of a level of thyroglobulin present in the exosome;
   diagnosing the subject with recurrent thyroid cancer for prognosis when the presence of thyroglobulin in the exosome shows an increasing trend,
   wherein the increasing trend is that within six months after the therapy of thyroid cancer, a serum thyroglobulin of the diagnosed subject is undetectable, while the urinary exosomal thyroglobulin of the diagnosed subject is detected at a level of 0.412 ng/mL to 9.29 ng/ml; and
   administering a thyroid cancer treatment to the diagnosed subject.

2. The method of claim 1, wherein the subject had been identified as a thyroid cancer patient.

3. The method of claim 1, wherein the therapy of thyroid cancer is selected from the group consisting of total thyroidectomy, partial thyroidectomy, thyroid remnant ablation with radioactive iodine, target therapy and a combination thereof.

4. The method of claim 1, further comprising isolating the exosome from the sample by size exclusion chromatography, density gradient centrifugation, differential centrifugation, nanomembrane ultrafiltration, immunoabsorbent capture, affinity purification, or microfluidic separation.

5. The method of claim 1, wherein the thyroid cancer treatment is selected from the group consisting of radioactive iodine, target therapy, and a combination thereof.

6. The method of claim 1, wherein the thyroid cancer is selected from the group consisting of follicular thyroid cancer, follicular variant papillary thyroid cancer, papillary thyroid cancer, medullary thyroid cancer, Hurthle cell cancer, anaplastic thyroid cancer, and a combination thereof.

7. The method of claim 6, wherein the thyroid cancer is follicular thyroid cancer or papillary thyroid cancer.

8. The method of claim 1, wherein the presence of thyroglobulin in the exosome is detected by peptide sequencing with mass spectrometry.

9. A method of evaluating a therapy of thyroid cancer, comprising:
   obtaining an exosome from a subject who had received the therapy of thyroid cancer, wherein the exosome is isolated from urine;
   detecting a trend of a level of thyroglobulin present in the exosome,
   wherein the level of thyroglobulin in the exosome is indicative of the efficacy of the therapy of thyroid cancer,
   wherein the thyroglobulin showing an increasing trend in the exosome is indicative of thyroid cancer recurrence,
   wherein the increasing trend is that within six months after the therapy of thyroid cancer, a serum thyroglobulin of the subject is undetectable, while the urinary exosomal thyroglobulin of the subject is detected at a level of 0.412 ng/ml to 9.29 ng/ml; and
   administering a thyroid cancer treatment to the subject when the presence of thyroglobulin in the exosome is detected.

10. The method of claim 9, wherein the therapy of thyroid cancer is selected from the group consisting of total thyroidectomy, partial thyroidectomy, thyroid remnant ablation with radioactive iodine, target therapy and a combination thereof.

11. The method of claim 9, wherein the thyroid cancer treatment is selected from the group consisting of radioactive iodine, target therapy, and a combination thereof.

\* \* \* \* \*

UNITED STATES PATENT AND TRADEMARK OFFICE
CERTIFICATE OF CORRECTION

PATENT NO. : 12,007,394 B2
APPLICATION NO. : 16/638157
DATED : June 11, 2024
INVENTOR(S) : Wang et al.

Page 1 of 1

It is certified that error appears in the above-identified patent and that said Letters Patent is hereby corrected as shown below:

On the Title Page

(71) Applicant should read:
(71) Applicant: NATIONAL TAIWAN UNIVERSITY, Taipei (TW)

Signed and Sealed this
Sixth Day of August, 2024

Katherine Kelly Vidal
*Director of the United States Patent and Trademark Office*